(12) United States Patent
Albert et al.

(10) Patent No.: US 10,638,941 B2
(45) Date of Patent: *May 5, 2020

(54) DISCORDANCE MONITORING

(71) Applicant: AliveCor, Inc.

(72) Inventors: David E. Albert, Oklahoma City, OK (US); Omar Dawood, San Francisco, CA (US); Ravi Gopalakrishnan, San Francisco, CA (US)

(73) Assignee: AliveCor, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/158,112

(22) Filed: Oct. 11, 2018

(65) Prior Publication Data
US 2019/0104948 A1    Apr. 11, 2019

Related U.S. Application Data

(63) Continuation of application No. 15/656,745, filed on Jul. 21, 2017, now Pat. No. 10,537,250, which is a continuation of application No. 15/154,849, filed on May 13, 2016, now Pat. No. 9,839,363.

(60) Provisional application No. 62/161,092, filed on May 13, 2015.

(51) Int. Cl.
| | | |
|---|---|---|
| *A61B 5/02* | (2006.01) | |
| *A61B 5/0205* | (2006.01) | |
| *A61B 5/00* | (2006.01) | |
| *A61B 5/024* | (2006.01) | |
| *A61B 5/11* | (2006.01) | |
| *A61B 5/046* | (2006.01) | |
| *A61B 5/0464* | (2006.01) | |
| *A61B 5/0408* | (2006.01) | |

(52) U.S. Cl.
CPC ............ *A61B 5/0205* (2013.01); *A61B 5/681* (2013.01); *A61B 5/7267* (2013.01); *A61B 5/02405* (2013.01); *A61B 5/02438* (2013.01); *A61B 5/046* (2013.01); *A61B 5/0464* (2013.01); *A61B 5/04085* (2013.01); *A61B 5/1118* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 7,846,106 B2 | 12/2010 | Andrews et al. | |
| 9,839,363 B2 * | 12/2017 | Albert | ................. A61B 5/0205 |
| 10,537,250 B2 * | 1/2020 | Albert | .................... A61B 5/681 |
| 2007/0213624 A1 | 9/2007 | Reisfeld et al. | |
| 2012/0109675 A1 | 5/2012 | Ziegler et al. | |
| 2012/0197148 A1 | 8/2012 | Levitan et al. | |
| 2012/0289790 A1 | 11/2012 | Jain et al. | |
| 2014/0125619 A1 | 5/2014 | Panther et al. | |
| 2014/0163393 A1 | 6/2014 | McCombie et al. | |

(Continued)

*Primary Examiner* — Ankit D Tejani
(74) *Attorney, Agent, or Firm* — Womble Bond Dickinson (US) LLP; William D. Jacobs, Jr.

(57) ABSTRACT

Described herein are systems, devices, and methods for cardiac monitoring. In particular, the systems, devices, and methods described herein may be used to conveniently sense the presence of an intermittent arrhythmia in an individual. The systems, devices, and methods described herein may be further configured to sense an electrocardiogram.

23 Claims, 7 Drawing Sheets

(56) References Cited

U.S. PATENT DOCUMENTS

| | | | |
|---|---|---|---|
| 2014/0276154 A1* | 9/2014 | Katra | A61B 5/04012 |
| | | | 600/509 |
| 2015/0057512 A1 | 2/2015 | Kapoor | |
| 2015/0122018 A1* | 5/2015 | Yuen | G01B 21/16 |
| | | | 73/384 |
| 2015/0305684 A1 | 10/2015 | Gross | |

* cited by examiner

DISCORDANCE MONITORING

CROSS-REFERENCE

This application is a continuation of U.S. patent application Ser. No. 15/656,745, filed Jul. 21, 2017, entitled "DISCORDANCE MONITORING", which is a continuation of U.S. patent application Ser. No. 15/154,849, filed May 13, 2016, entitled "DISCORDANCE MONITORING", now issued as U.S. Pat. No. 9,839,363 on Dec. 12, 2017, which claims the benefit of U.S. Provisional Application No. 62/161,092, filed May 13, 2015, both of which are incorporated herein by reference in its entirety.

BACKGROUND

Irregular heartbeats and arrhythmias are associated with significant morbidity and mortality in patients. Arrhythmias may occur continuously or may occur intermittently. Types of arrhythmia include atrial fibrillation and supraventricular tachycardia. Non-invasive cardiac monitoring is useful in diagnosing cardiac arrhythmia.

SUMMARY

Described herein are systems, devices, and methods for cardiac monitoring. The systems, devices, and methods described herein for cardiac monitoring may comprise portable computing devices such as smartphones, smartwatches, laptops, and tablet computers. Cardiac monitoring using the systems, devices, and methods described herein may be used to predict or identify the occurrence of arrhythmias.

Arrhythmias may occur continuously or may occur intermittently. Continuously occurring arrhythmias may be diagnosed using a number of different techniques including, for example, palpating a radial pulse of an individual, auscultating heart sounds of an individual, recording a heart rate of an individual, and recording an electrocardiogram of an individual. Because a continuous or essentially continuous arrhythmia is always present or essentially always present in the patient, any of the aforementioned diagnosis techniques may be applied at any time in order to make a diagnosis. For intermittent arrhythmia diagnosis any of the aforementioned diagnosis techniques may also be used, however, because intermittent arrhythmias do not always present, the diagnostic technique cannot be applied at any time, but must be applied at the time when the individual is experiencing the arrhythmia. Thus, diagnosing, intermittent arrhythmias may be difficult, because, for example, it is not practical to be prepared to apply one of the aforementioned diagnostic modalities at the exact time that an individual experiences an intermittent arrhythmia. This particular difficulty may also be compounded when an individual is not aware that they are experiencing an intermittent arrhythmia so that they would not, for example, seek out a health care provider during the intermittent arrhythmia.

However, certain parameter values may be conveniently sensed continuously such as, for example, heart rate and activity level, and analyzed to predict or determine the presence of an arrhythmia. One or more conveniently continuously sensed parameter values such as, for example, heart rate and activity level may be analyzed to determine the future onset of or the presence of an arrhythmia by identifying discordance between these two parameter values. For example, discordance between two sensed values may indicate the future onset of or the presence of an arrhythmia. In response to the identification of the future onset of or presence of an arrhythmia an electrocardiogram may be caused to be sensed.

Additional sensed parameters may also be used in an analysis as part of the cardiac monitoring systems, devices, and methods described herein. For example, a determined heart rate variability may be compared to a sensed heart rate and activity level to determine the presence of, for example, atrial fibrillation or supraventricular tachycardia.

Described herein is a method for cardiac monitoring, comprising: sensing an activity level value of an individual with a first sensor of a wearable device worn by said individual; sensing a heart rate value of said individual with a second sensor of said wearable device; determining a heart rate variability value with a processor of said wearable device; determining if a discordance is present between two or more of said activity level value, said heart rate value, and said heart rate variability value with said processor; and indicating to said individual with said wearable device to record an electrocardiogram when said discordance is determined to be present. In some embodiments, said first sensor comprises an accelerometer. In some embodiments, said first sensor comprises a gyroscope. In some embodiments, said second sensor comprises a photosensor. In some embodiments, said discordance is determined to be present when said activity level value is normal and said heart rate value is elevated. In some embodiments, said discordance is determined to be present when said activity level value is normal, said heart rate value is elevated, and said heart rate variability value is increased. In some embodiments, said method comprises indicating a presence of atrial fibrillation. In some embodiments, said discordance is determined to be present when said activity level value is normal, said heart rate value is elevated, and said heart rate variability value is decreased. In some embodiments, said method comprises indicating a presence of a supraventricular tachycardia. In some embodiments, setting one or more threshold values based on said activity level value, said heart rate value, and said heart rate variability value. In some embodiments, said one or more threshold values is determined using a machine learning algorithm.

Described herein is wearable device for cardiac monitoring, comprising: a processor; a first sensor configured to sense an activity level value of an individual, wherein said first sensor is coupled to said processor; a second sensor configured to sense a heart rate value of an individual, wherein said second sensor is coupled to said processor; a first electrode and a second electrode configured to sense an electrocardiogram; a non-transitory computer readable storage medium encoded with a computer program including instructions executable by said processor to cause said processor to: determine if a discordance is present between said activity level value of said individual and said heart rate value of said individual; and indicate that said electrocardiogram be recorded when said discordance is determined to be present. In some embodiments, said first sensor comprises an accelerometer. In some embodiments, said first sensor comprises a gyroscope. In some embodiments, said second sensor comprises a photosensor. In some embodiments, said discordance is determined to be present when said activity level value is normal and said heart rate value is elevated. In some embodiments, said computer program includes instructions that cause said processor to determine a heart rate variability value. In some embodiments, said discordance is determined to be present when said activity level value is normal, said heart rate value is elevated, and said heart rate variability value is increased. In some embodiments, said computer program includes instructions that cause said processor to indicate a presence of atrial fibrillation. In some embodiments, said discordance is determined to be present when said activity level value is normal, said heart rate value is elevated, and said heart rate variability value is elevated. In some embodiments, said computer program includes instructions that cause said processor to indicate a presence of a supraventricular tachycardia. In some embodiments, said computer program includes instructions that cause said processor to set one or more threshold values based on said activity level value, and said heart rate value.

In some embodiments, said one or more threshold values is determined using a machine learning algorithm.

Described herein is a method for cardiac monitoring, comprising: sensing an activity level value of an individual with a first sensor of a wearable device worn by said individual; sensing a heart rate value of said individual with a second sensor of said wearable device; determining if a discordance is present between two or more of said activity level value and said heart rate value by using an activity level threshold and a heart rate threshold with a processor of said wearable device; and adjusting said activity level threshold and said heart rate level threshold using a machine learning algorithm executed by said processor.

BRIEF DESCRIPTION OF THE DRAWINGS

The novel features of the individual matter described herein are set forth with particularity in the appended claims. A better understanding of the features and advantages of the present individual matter described herein will be obtained by reference to the following detailed description that sets forth illustrative embodiments, in which the principles of the individual matter described herein are utilized, and the accompanying drawings of which:

DETAILED DESCRIPTION

Cardiac Monitoring

Described herein are systems, devices, and methods for use in cardiac monitoring. Cardiac monitoring typically comprises monitoring of the heart function of an individual for changes in, for example, heart rate or heart rhythm.

Heart rate may vary between, for example, bradycardia which typically is defined as a heart rate of less than 60 beats per minute, normal resting heart rate which typically is defined as a heart rate of between 60-100 beats per minute, and tachycardia which typically is defined as a heart rate of greater than 100 beats per minute. Variance of heart rate over a period of time may be referred to as Heart Rate Variability (HRV).

Heart function is also measured in terms of regularity of rhythm. A normal heart rhythm comprises of a systole (ejection phase) and diastole (filling phase). During the phases of systole and diastole, the ventricles of the heart act in concert in a regular manner that is repeated with every single heartbeat. When there is an abnormality of rhythm, the condition is typically referred to as an arrhythmia. Examples of arrhythmias include atrial fibrillation, WPW syndrome, prolonged QT syndrome, and premature ventricular contractions.

Many arrhythmias occur intermittently and relatively infrequently. Thus, in order to monitor and capture an intermittent arrhythmia, continuous monitoring is typically required. ECGs can be measured continuously in the ambulatory patient using holter monitoring, but this type of monitoring is cumbersome for the patient and is thus not widely used. A device or system configured to take an intermittent ECG is much more convenient for users. Such devices or systems comprise a mobile computing device that includes one or more electrodes that sense an ECG when contacted by a skin surface of the patient. Such devices are light and portable and don't necessarily require the user to be in continuous physical contact with one or more electrodes as they would with a holter type monitor. Intermittent arrhythmias can be recorded with these devices and systems when a user is given an indication that an intermittent arrhythmia is occurring. HRV sensing is used in combination with these devices or systems to indicate to a user when to contact one or more electrodes in order to sense an ECG.

Figure 1:
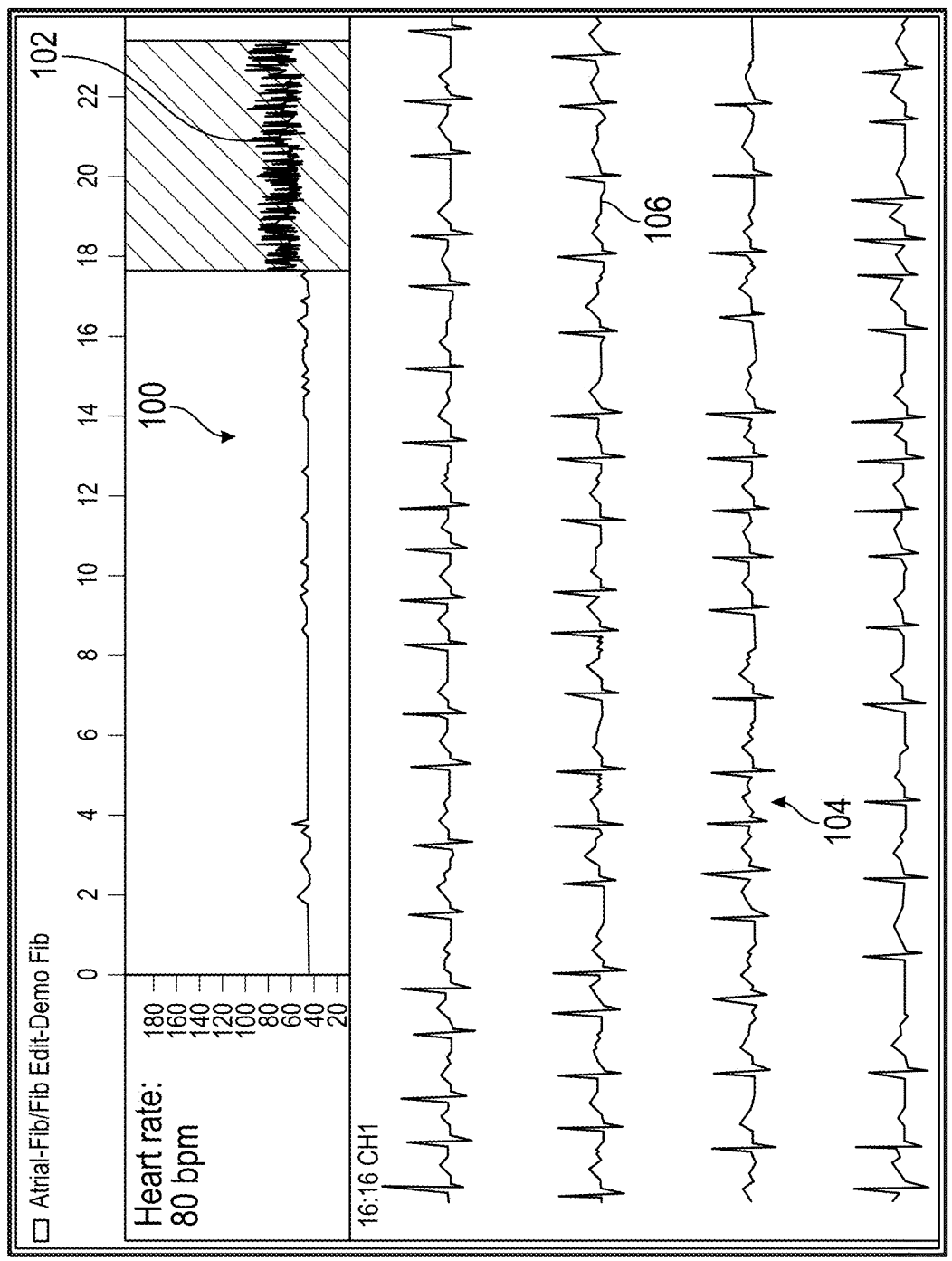
FIG. 1 shows a heart rate tracing with a corresponding electrocardiogram (ECG) tracing both sensed from the same individual over the same period.

FIG. 1 shows a heart rate tracing 100 with a corresponding electrocardiogram (ECG) tracing 104 both sensed from the same individual over the same period. As is shown in the ECG tracing 104, the individual experienced a period of intermittent atrial fibrillation 106 during the time that the ECG was sensed. As is also shown in the heart rate tracing 100, the heart rate of the individual rapidly increased 102 during the period of intermittent atrial fibrillation. As such, the HRV of the individual increased during the period of intermittent atrial fibrillation as the heart rate of the individual increased from a resting heart rate to an increased heart rate 102. HRV changes are therefore associated with atrial fibrillation, wherein increased HRV is found during periods of intermittent atrial fibrillation.

Figure 2:
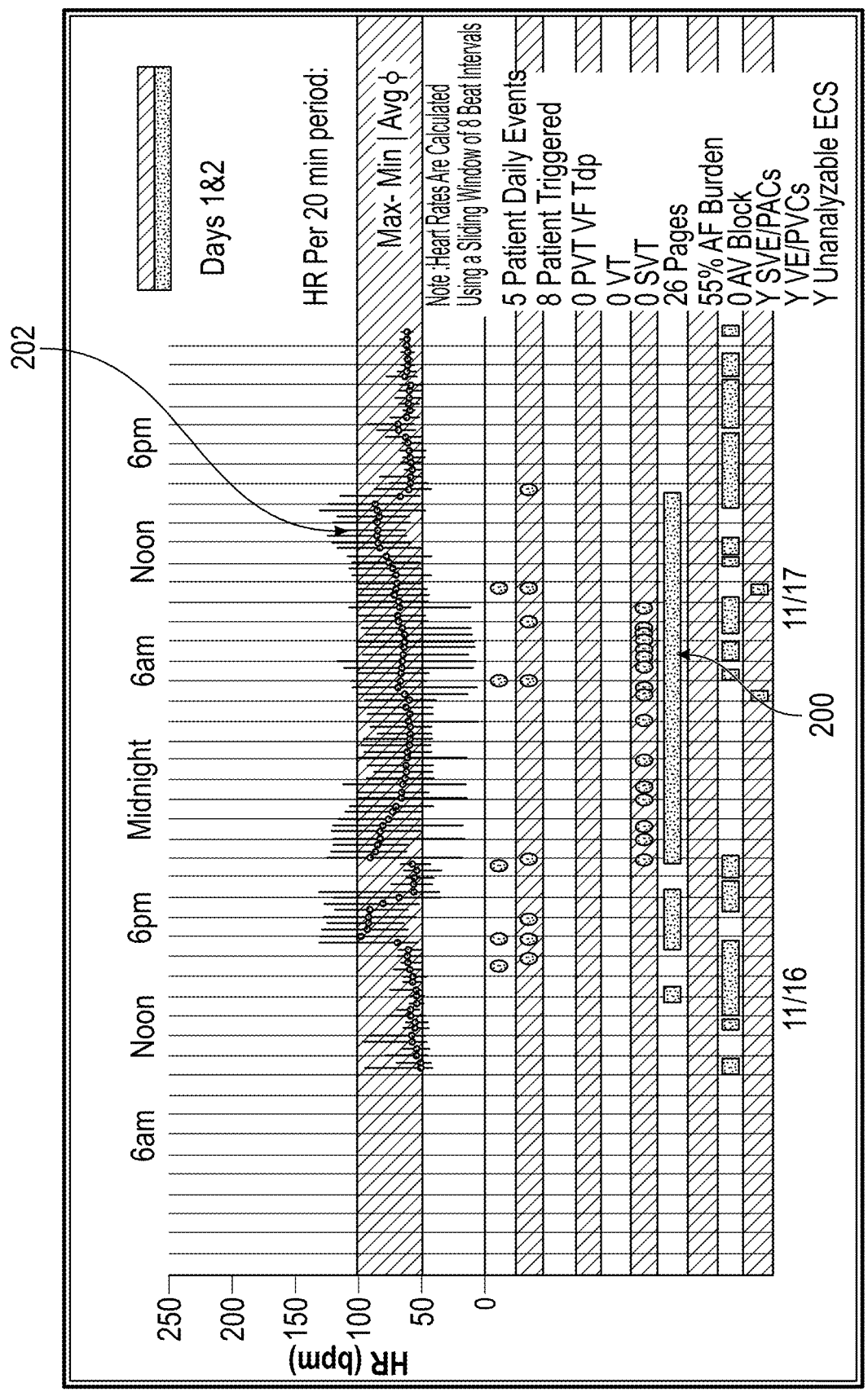
FIG. 2 shows a graphic showing both heart rate and rhythm analysis over a period of time in an individual who experienced different arrhythmias.

FIG. 2 shows a graphic showing both heart rate 202 and rhythm analysis 200 over a period of time in an individual who experienced different arrhythmias. As shown, the measured heart rate 202 tended to increase above 100 beats per minute during the periods of sensed atrial fibrillation 200. Thus, elevated heart rate above resting heart rate occurred in this individual during the period of arrhythmia.

Figure 3:
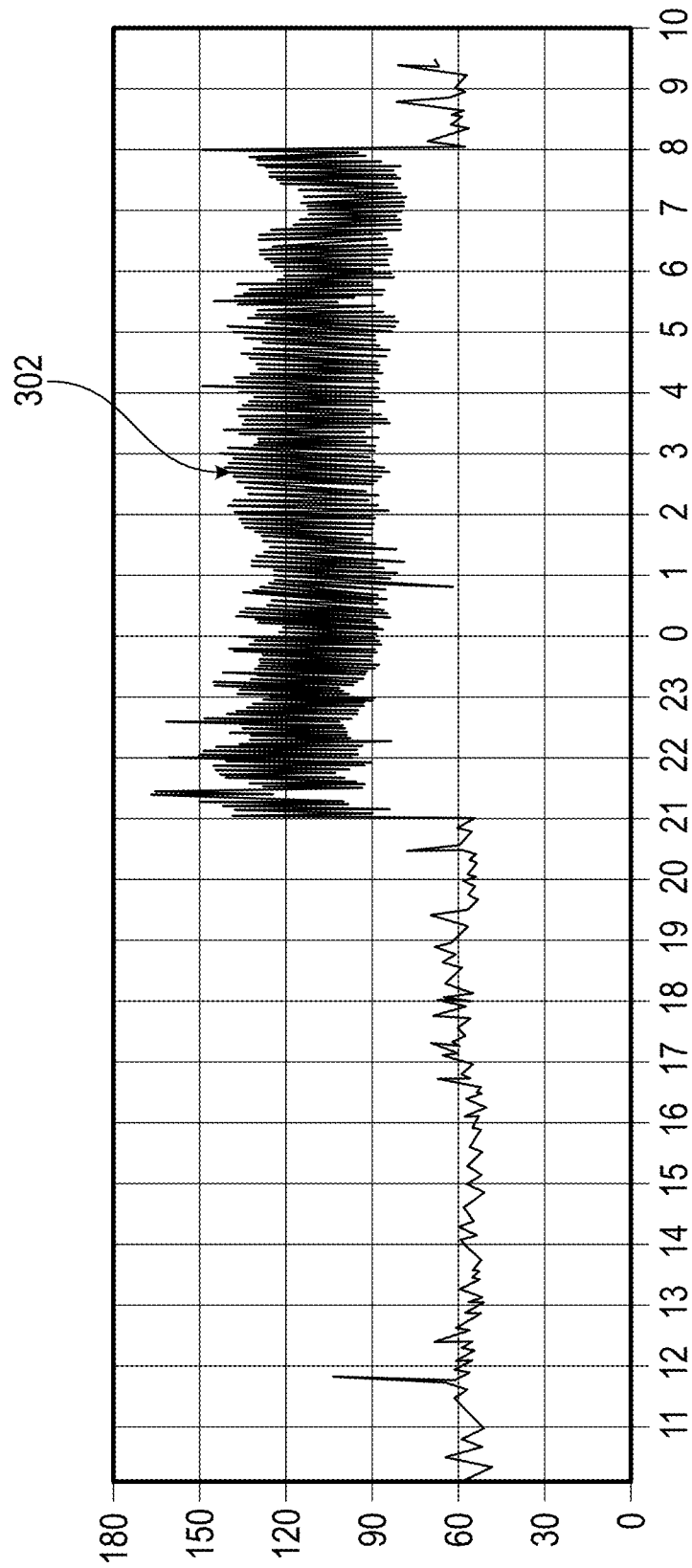
FIG. 3 shows a close up of a heart rate tracing sensed over a period of paroxysmal atrial fibrillation.

FIG. 3 shows a close up of a heart rate tracing sensed over a period of paroxysmal atrial fibrillation. As shown, there was a substantial step increase from a normal heart of between 60-100 beats per minute to above 100 beats per minute 302 during the period of atrial fibrillation.

Figure 4:
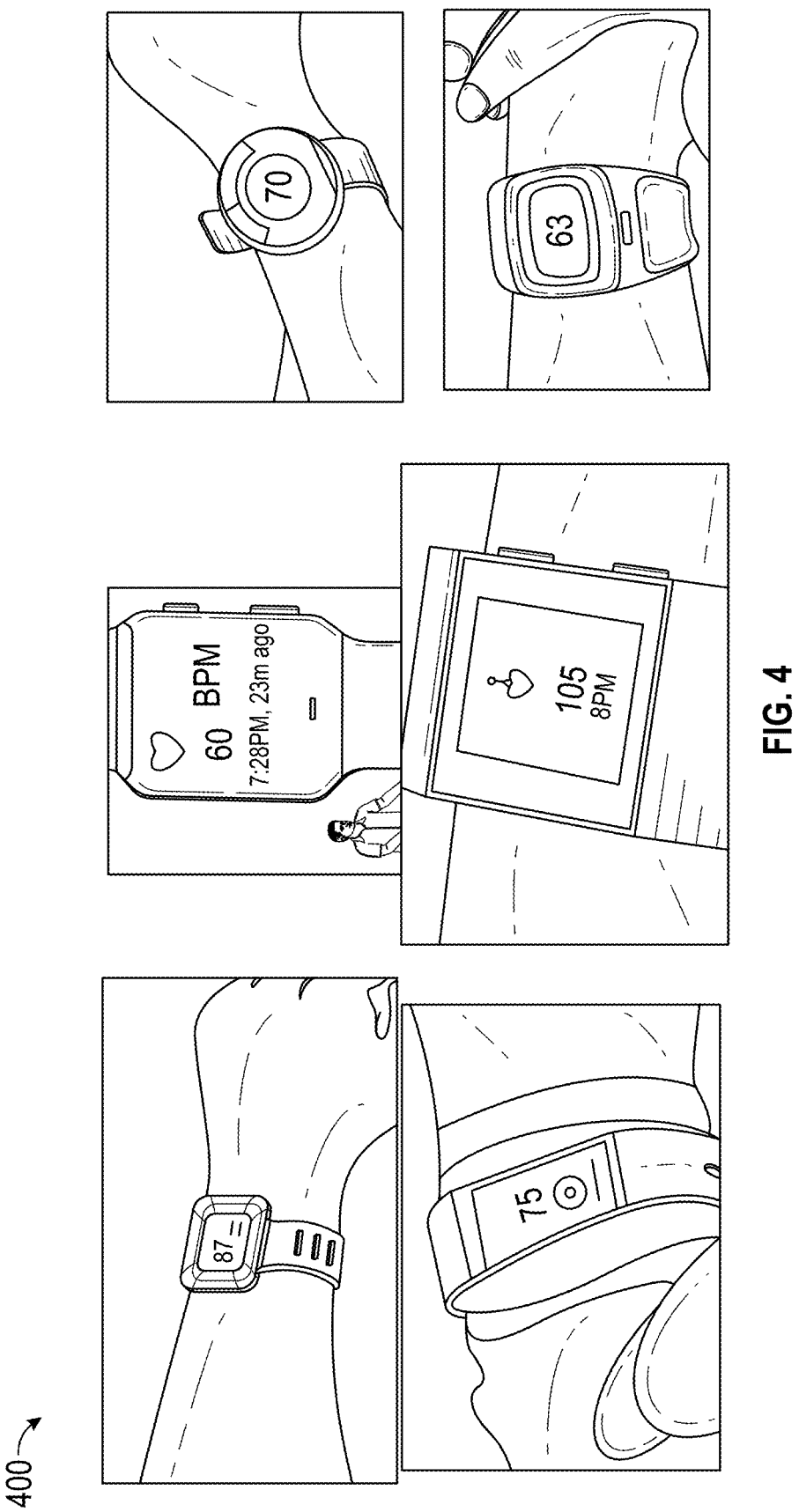
FIG. 4 shows available technologies for continuously sensing a heart rate or an activity level.

FIG. 4 shows available technologies 400 for continuously sensing a heart rate or an activity level. Shown are smartwatches made available by manufactures such as, for example, Apple. A wearer of one of the shown smartwatch technologies 400 may conveniently and continuously wear one or more sensors that are either coupled to or integrated with the watch throughout the day, thus, effectively continuously monitoring one or more parameter values via the one or more sensors that are either coupled to or integrated with the smartwatch. Thus, one of the smartwatch technologies 400 are an example of a type of device in the form of a wearable that conveniently provides continuous monitoring of one or more parameters of a user. Non-limiting examples of wearable devices that may have one or more sensors either coupled to them or integrated with them include watches (e.g. smartwatches), eyeglasses, wristbands, necklaces, and clothing. The one or more continuously sensed parameters of the user of such a technology as, for example, shown in FIG. 4, are then used to indicate to the user to use a device or system to sense an ECG. For example, a user wearing a smartwatch having a heart rate sensor is alerted by the smartwatch to record an ECG when the HRV of the user increases.

Figure 5:
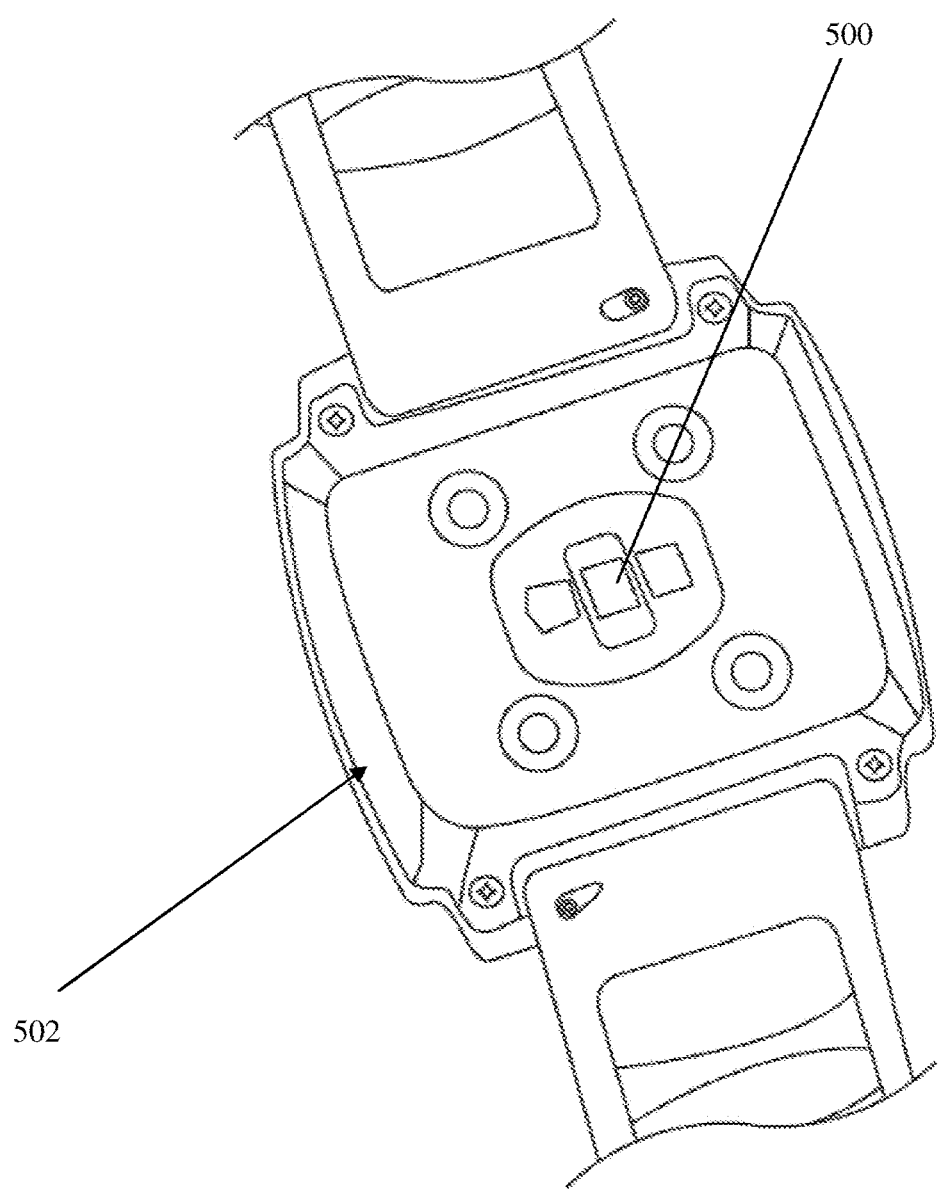
FIG. 5 shows a photosensor commonly used to measure heart rates integrated with a smartwatch.

FIG. 5 shows a photosensor 500 commonly used to measure heart rates integrated with a smartwatch 502.

Activity level is correlated with arrhythmia in many individuals who have a predisposition to develop arrhythmia wherein increased activity level is associated with onset of arrhythmia. In other individuals an increased activity level that is detected by one or more activity sensors in the presence of increased HRV is likely normal and is not associated with arrhythmia. Thus, as described herein, the addition of continuous heart rate monitoring along with continuous activity level monitoring may achieve the same results, in terms of arrhythmia monitoring, as continuous electrocardiogram monitoring. Using one or more sensors associated with the devices or systems described herein two parameter values of heart rate and activity level may be conveniently and accurately continuously and simultaneously sensed.

Devices and Systems

Figure 6:
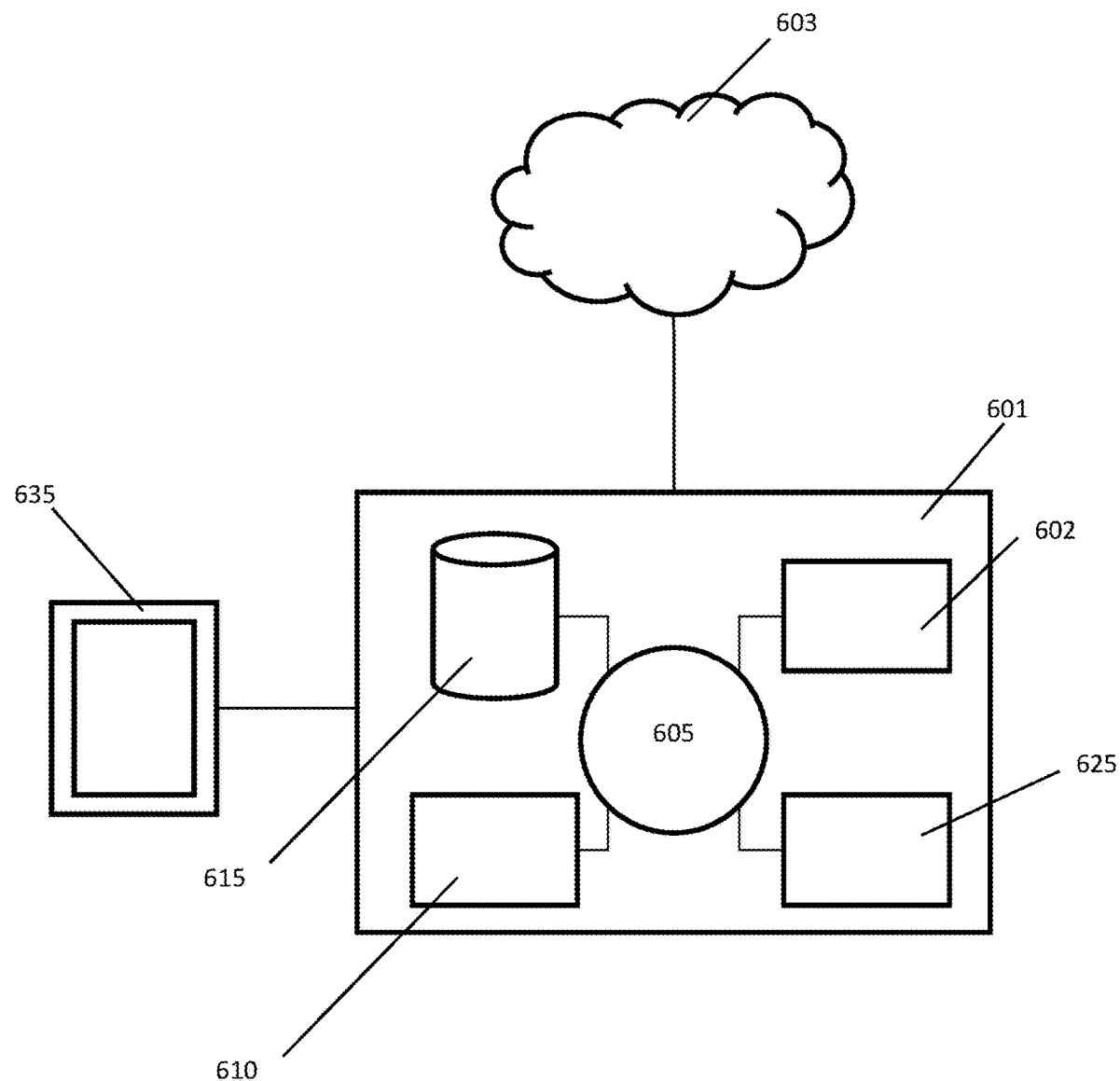
FIG. 6 exemplifies a computer system that is programmed or otherwise configured to sense one or more physiologic parameters of an individual.

FIG. 6 exemplifies a computer system 601 that is programmed or otherwise configured to sense one or more physiologic parameters of an individual. Non-limiting examples of physiologic parameters include heart rate, blood pressure, temperature, oxygen saturation, ECG, HRV, and activity level. The computer system 601 comprises an electronic device of a user 635, or comprises a computer system that is remotely located with respect to the electronic device 635. Electronic devices suitable for use with the system 601 include mobile electronic devices such as smartphones, smartwatches, tablets, and laptops. The electronic device 601 comprises one or more sensors configured to sense a physiologic parameter. Numerous sensors are known for measuring heart rate. Non-limiting examples of suitable sensors include light based sensors such as, for example, infrared sensor/emitter, ultrasound sensors, and tactile sensors. Sensors for measuring rhythm include electrodes for measuring electrocardiograms (ECG) and light based sensors for measuring photoplethysmograms.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 602 (e.g., network adapter) for communicating with one or more other systems, and peripheral devices 625, such as cache, other memory, data storage and/or electronic display adapters. The memory 610, storage unit 615, interface 602 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 603 with the aid of the communication interface 602. The network 603 can be the Internet, an internet and/or extranet, or an intranet and/or extranet that is in communication with the Internet. The network 603 in some cases is a telecommunication and/or data network. The network 603 can include one or more computer servers, which can enable distributed computing, such as cloud computing. The network 603, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 603. For instance, the computer system 601 can communicate with a remote computer system of a user (e.g., mobile device, server, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 603.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution The computer system 601 can include or be in communication with an electronic display 535 that comprises a user interface (UI) 640 for providing, for example, distributions of magnetic fields, distributions of electrical currents, distributions of local myocardial activities, etc. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm, for example, is used to analyze a sensed physiologic parameter.

A device as described herein is in some embodiments configured to sense two or more physiologic parameters. For example, a device configured to measure the heart rate of an individual as described herein is also in some embodiments configured to sense the electrocardiogram of said individual. In these embodiments, a device as described herein includes one or more electrodes configured to sense an electrocardiogram of an individual. In some embodiments, a device as described herein comprises two electrodes. In some embodiments, a device as described herein comprises three electrodes. In some embodiments, a device as described herein comprises four electrodes. In some embodiments, a device as described herein comprises five electrodes. In some embodiments, a device as described herein comprises six electrodes. In some embodiments, a device as described herein comprises seven electrodes. In some embodiments, a device as described herein comprises eight electrodes. In some embodiments, a device as described herein comprises nine electrodes. In some embodiments, a device as described herein comprises ten electrodes. Electrodes of the device described herein are configured to sense an electrocardiogram of an individual and transmit the sensed electrocardiogram data to a processor integrated with the device or part of the system described herein. In some embodiments, the processor is configured to display the electrocardiogram on a display of the device described herein. In some embodiments, the device is configured to sense and/or display a single lead electrocardiogram. In some embodiments, the single lead comprises any of Lead I, Lead II, Lead aVR, Lead aVL, Lead aVF, Lead V1, Lead V2, Lead V3, Lead V4, Lead V5, and Lead V6. In some embodiments, the device is configured to sense and/or display two leads comprising any two of Lead I, Lead II, Lead aVR, Lead aVL, Lead aVF, Lead V1, Lead V2, Lead V3, Lead V4, Lead V5, and Lead V6. In some embodiments, the device is configured to sense and/or display two leads comprising any three of Lead I, Lead II, Lead aVR, Lead aVL, Lead aVF, Lead V1, Lead V2, Lead V3, Lead V4, Lead V5, and Lead V6. In some embodiments, the device is configured to sense and/or display three leads comprising any three of Lead I, Lead II, Lead aVR, Lead aVL, Lead aVF, Lead V1, Lead V2, Lead V3, Lead V4, Lead V5, and Lead V6. In some embodiments, the device is configured to sense and/or display four leads comprising any four of Lead I, Lead II, Lead aVR, Lead aVL, Lead aVF, Lead V1, Lead V2, Lead V3, Lead V4, Lead V5, and Lead V6. In some embodiments, the device is configured to sense and/or display five leads comprising any five of Lead I, Lead II, Lead aVR, Lead aVL, Lead aVF, Lead V1, Lead V2, Lead V3, Lead V4, Lead V5, and Lead V6. In some embodiments, the device or system is configured to sense and/or display six leads comprising any six of Lead I, Lead II, Lead aVR, Lead aVL, Lead aVF, Lead V1, Lead V2, Lead V3, Lead V4, Lead V5, and Lead V6. In some embodiments, the device is configured to sense and/or display seven leads comprising any seven of Lead I, Lead II, Lead aVR, Lead aVL, Lead aVF, Lead V1, Lead V2, Lead V3, Lead V4, Lead V5, and Lead V6. In some embodiments, the device is configured to sense and/or display eight leads comprising any eight of Lead I, Lead II, Lead aVR, Lead aVL, Lead aVF, Lead V1, Lead V2, Lead V3, Lead V4, Lead V5, and Lead V6. In some embodiments, the device is configured to sense and/or display nine leads comprising any nine of Lead I, Lead II, Lead aVR, Lead aVL, Lead aVF, Lead V1, Lead V2, Lead V3, Lead V4, Lead V5, and Lead V6. In some embodiments, the device is configured to sense and/or display ten leads comprising any ten of Lead I, Lead II, Lead aVR, Lead aVL, Lead aVF, Lead V1, Lead V2, Lead V3, Lead V4, Lead V5, and Lead V6. In some embodiments, the device is configured to sense and/or display eleven leads comprising any eleven of Lead I, Lead II, Lead aVR, Lead aVL, Lead aVF, Lead V1, Lead V2, Lead V3, Lead V4, Lead V5, and Lead V6. In some embodiments, the device is configured to sense and/or display twelve leads comprising any twelve of Lead I, Lead II, Lead aVR, Lead aVL, Lead aVF, Lead V1, Lead V2, Lead V3, Lead V4, Lead V5, and Lead V6. In some embodiments, the device includes software configured to cause a processor of said device to analyze the sensed electrocardiogram. An analysis of a sensed electrocardiogram performed by the processor of the device identifies the presence of an abnormal heart condition. For example, an analysis performed by a processor of a device, in some embodiments, identifies arrhythmias by, for example, analysis of the PQRST waveform and/or comparing multiple PQRST waveforms within an electrocardiogram. In some embodiments, the processor carries out an analysis of an electrocardiogram by comparing one or more PQRST waveforms of an individual against a one or more PQRST waveforms of other individuals from a database containing electrocardiograms of other individuals. In some embodiments of the devices described herein, an individual is alerted to sense an electrocardiogram by, for example, engaging one or more electrodes when the device senses one or more physiologic parameters. For example, in some embodiments, a device as described herein is configured to sense a blood pressure of an individual, and in some of these embodiments, the device is configured to sense a second physiologic parameter of the individual such as for example a heart rate. An accelerated heart rate of an individual sensed by the device in addition to, for example, a low blood pressure of the individual concurrently sensed by the device, triggers the processor of the device to indicate to the individual to engage with the electrodes of the device in order to sense an electrocardiogram.

The combination of a sensed accelerated heart rate and low blood pressure typically indicate an abnormality, however, other physiologic conditions may also produce an elevated heart rate accompanied by low blood pressure including, for example, dehydration. Thus, in some embodiments, accuracy is enhanced when physiologic parameters such as, for example, heart rate, blood pressure, oxygen saturation, and temperature are compared to baseline values of the individual or to a data from a database containing the physiological parameters of other individuals. Some elite athletes, for example, have physiologic parameter values that would be abnormal in another individual such as, for example, very low heart rates or increased heart rate variability (e.g. during a period of exercise).

A device as described herein is in some embodiments configured to sense a photophletysmogram of an individual. A photopletysmogram, for example, provides cardiac cycle information and may, for example, be analyzed by a processor of a device described herein to determine a presence of a premature ventricular contraction.

In some embodiments, a device as described herein is configured to sense a pulse oxygenation of an individual. A device as described herein is configured to sense a pulse oxygenation of an individual in some embodiments.

Analysis

In some embodiments, a device as described herein is configured to sense and/or analyze a number of additional physiologic parameters. Non-limiting examples of parameter values sensed and/or analyzed by the devices and systems described herein include heart rate, activity level, blood pressure, temperature, pulse oxygen, and heart rate variability. Analysis includes in some embodiments the comparison of a first sensed physiologic parameter to a second sensed physiologic and determining if a discordance exists between the first and second sensed parameter values.

In some embodiments, a device as described herein is configured to monitor for arrhythmia in an individual, wherein monitoring may comprise the identification of onset of an arrhythmia. In some embodiments, cardiac monitoring carried out by the devices described herein comprises, for example, monitoring for the presence or onset of arrhythmia in an individual who has not previously been identified to have an arrhythmia. In some embodiments, cardiac monitoring carried out by the devices described herein comprises the identification of onset of a known or suspected intermittent arrhythmia. In some embodiments, the devices described herein are configured to predict an onset of an arrhythmia in an individual. The onset of an arrhythmia is, for example, predicted due to a sudden and significant shift in the value of a sensed physiologic parameter such as heart rate. A prediction of arrhythmia is more accurate when two or more physiologic parameters are concurrently sensed and analyzed with respect to one another. For example, sensing of heart rate changes with respect to a sensed activity level provides contextual information for the sensed heart rate.

A subset of arrhythmias are sometimes termed tachyarrhythmias. Tachyarrhythmias typically comprise a tachycardic heart rate which may comprise a heart rate above 100 beats per minute. Tachyarrhythmias may comprise, for example, certain types of atrial fibrillation and supraventricular tachycardia. In some embodiments, the devices as described herein are configured to identify the presence or onset of a tachyarrhythmia, such as, for example, atrial fibrillation or supraventricular tachycardia. In some embodiments, the devices as described herein are configured to identify the presence or onset of a tachyarrhythmia. In some embodiments, the devices as described herein are configured to predict the onset of a tachyarrhythmia.

In some embodiments, the devices as described herein are configured to provide continuous cardiac monitoring. In some embodiments, the devices as described herein are configured to provide continuous cardiac monitoring for a period of up to one year. In some embodiments, the devices as described herein are configured to provide continuous cardiac monitoring for a period of up to 12 months. In some embodiments, the devices described herein are configured to provide continuous cardiac monitoring for a period of up to 6 months. In some embodiments, the devices described herein are configured to provide continuous cardiac monitoring for a period of up to 3 months. In some embodiments, the devices described herein are configured to provide continuous cardiac monitoring for a period of up to 1 month. In some embodiments, the devices described herein are configured to provide continuous cardiac monitoring for a period of up to 2 weeks. In some embodiments, the devices described herein are configured to provide continuous cardiac monitoring for a period of up to 1 weak. In some embodiments, the devices described herein are configured to provide continuous cardiac monitoring for a period of up to 72 hours. In some embodiments, the devices described herein are configured to provide continuous cardiac monitoring for a period of up to 48 hours. In some embodiments, the devices described herein are configured to provide continuous cardiac monitoring for a period of up to 24 hours. In some embodiments, the devices described herein are configured to provide continuous cardiac monitoring for a period of up to 12 hours. In some embodiments, the devices described herein are configured to provide continuous cardiac monitoring for a period of up to 8 hours. In some embodiments, the devices described herein are configured to provide continuous cardiac monitoring for a period of up to 4 hours. In some embodiments, the devices described herein are configured to provide continuous cardiac monitoring for a period of up to 2 months.

In some embodiments, the devices described herein are configured to provide intermittent cardiac monitoring. In some embodiments, intermittent cardiac monitoring is initiated in response to one or more sensed parameter values. Non-limiting examples of the one or more sensed parameter value that may cause initiation of intermittent cardiac monitoring may comprise, for example, a heart rate of an individual, a blood pressure of an individual, an activity level an individual, a temperature of an individual, a pulse oximetry of an individual, or any other sensed biometric parameter of an individual. In some embodiments, an electrocardiogram of an individual may be sensed in response to one or more sensed parameters. For example, an electrocardiogram may be caused to be sensed in response to a heart rate value.

In some embodiments, one or more continuous sensors may sense one or more parameters that cause the initiation of intermittent cardiac monitoring by one or more sensors. In some embodiments, a heart rate of an individual is sensed continuously. In some embodiments, an activity level of an individual is sensed continuously. In some embodiments, a heart rate variability of an individual is sensed continuously. In some embodiments, an electrocardiogram of an individual is sensed intermittently. In some embodiments, an intermittently sensed electrocardiogram is caused to be sensed in response to a continuously measured heart rate of an individual. In some embodiments, an intermittently sensed electrocardiogram is caused to be sensed in response to an activity level of an individual. In some embodiments, an intermittently sensed electrocardiogram is caused to be sensed in response to both a continuously measured heart rate and a continuously measured activity level. In some embodiments, an intermittently sensed electrocardiogram is caused to be sensed in response to a continuously sensed heart rate, a continuously sensed activity level, and a continuously sensed heart rate variability.

In some embodiments, a device or system as described herein comprises one or more sensors configured for continuous cardiac monitoring. In some embodiments, a device or system as described herein comprises one or more sensors configured for intermittent cardiac monitoring. In some embodiments, a device or system as described herein comprises one or more heart rate sensors, which may, for example, comprise a photosensor. In some embodiments, a device or system as described herein comprises one or more activity level sensors, which may, for example, comprise an accelerometer or a gyroscope. In some embodiments, a device or system as described herein comprises one or more electrocardiogram sensors, which may, for example, comprise one or more electrodes. Non-limiting examples of other sensors suitable for use with the devices, systems, and methods described herein further comprise blood pressure sensors, temperature sensors, and pulse oximetry sensors.

In some embodiments, a device or system as described herein comprises a processor. In some embodiments, a process is coupled with one or more sensors that are configured to sense continuously and one or more sensors that are configured to sense intermittently. In some embodiments, a processor is configured to receive parameter values from one or more sensors. In some embodiments, a processor is configured to activate one or more sensors or to initiate the sensing of a parameter value. In some embodiments, a processor is configured to analyze a parameter value. In some embodiments, a processor is configured to compare a first parameter value with a second parameter value. In some embodiments, a first and a second parameter value to be compared are simultaneously or essentially simultaneously sensed.

In some embodiments, a device or system as described herein further comprises software in the form of a program or application. In some embodiments, the program or application may be configured to cause a processor to carry out one or more functions. In some embodiments, the program or application may be configured to cause a processor to receive parameter values from one or more sensors. In some embodiments, the program or application may be configured to cause a processor to activate one or more sensors or to initiate the sensing of a parameter value. In some embodiments, the program or application may be configured to cause a processor to analyze a parameter value. In some embodiments, the program or application may be configured to cause a processor to compare a first parameter value with a second parameter value. In some embodiments, a first and a second parameter value to be compared are simultaneously or essentially simultaneously sensed.

In some embodiments, the devices described herein are configured to carry out an analysis, wherein the analysis is performed by a processor. In some embodiments, an analysis of one or more parameter values carried out by the devices described herein comprises a comparison of a sensed parameter value to a threshold or range. For example, an analysis may comprise determining whether a sensed heart rate value falls within one or more ranges. For example, in some embodiments, a sensed heart rate may be determined to be within a heart rate range comprising a range between 60-100 beats per minute. For example, in some embodiments, a sensed heart rate may be determined to be in a heart rate range comprising a range of values less than 60 beats per minute. For example, in some embodiments, a sensed heart rate may be determined to be within a heart rate range comprising a range of values above 100 beats for minute.

In some embodiments, an analysis of one or more parameter values carried out by the devices described herein comprises a comparison of a first sensed parameter to a second sensed parameter. For example, in some embodiments, a heart rate value is compared to a sensed activity level of an individual.

In some embodiments, a first sensed value is compared to a second sensed value, and it is determine whether a discordance exists between the two values. For example, in some embodiments, an elevated heart rate value would be expected to be present during a period of elevated activity, thus an elevated heart rate and an elevated activity level that are simultaneously sensed would not be found to be in discordance with one another.

A discordance may be identified when a first sensed parameter value would not be expected to coincide with a second sensed parameter value. For example, an elevated heart rate value would not be expected to be present with a normal or resting activity level and thus the two values are in discordance with one another. For example, in some embodiments, when a heart rate sensor senses a heart rate above 100 beats per minute and a simultaneously sensed activity level is determined to be a resting activity level, an analysis of the two sensed values determines that they are in discordance with one another.

In some embodiments, an analysis carried out by the devices and systems described herein comprises the determination of an increase in a heart rate variability. In some embodiments, an analysis carried out by the devices and systems described herein comprises comparing a heart rate variability with one or more sensed parameter values. For example, in some embodiments, a heart rate variability is compared to concurrently or essentially concurrently sensed heart rate and activity level values.

In some embodiments, an analysis carried out by the devices and systems described herein comprises the prediction of or the identification of the initiation of an arrhythmia using an identified discordance as described herein. In some embodiments, a discordance comprising a simultaneously or essentially simultaneously sensed elevated heart rate and resting or normal activity level is determined to indicate the imminent initiation of an arrhythmia or the presence of an arrhythmia. In particular, because the heart rate is elevated, the arrhythmia with this type of discordance typically comprises a tachyarrhythmia.

In some embodiments, a simultaneously sensed increase in heart rate variability, an elevated heart rate, and a resting or normal activity rate is determined to indicate the future onset or presence of atrial fibrillation. In some embodiments, a sensed increased heart rate variability, normal resting heart rate, and resting or normal activity rate may also be determined to indicate the future onset of or the presence of atrial fibrillation. In some embodiments, a simultaneously sensed decrease in heart rate variability, an elevated heart rate, and a resting or normal activity rate is determined to indicate the future onset or presence of supraventricular tachycardia. In some embodiments, when an arrhythmia is determined to be imminent or present, an electrocardiogram is recorded. In some embodiments, an individual is instructed or signaled by a cardiac monitoring device or system described herein to engage one or more electrodes in order to sense in electrocardiogram. In some embodiments, one or more electrodes may be positioned on a surface of a cardiac monitoring device so that the individual may, for example, comfortably engage a first electrode with a skin surface of a first extremity while simultaneously engaging a second electrode with a skin surface of a second extremity. In some embodiments, one or more electrodes may be affixed to an individual's body and are automatically engaged to sense an electrocardiogram by a cardiac monitoring device or system when an arrhythmia is determined to be imminent or present in the individual. For example, a first electrode may be positioned on smartwatch worn by the individual on a first extremity and a second electrode may be positioned on a wristlet worn by the individual on a second extremity. In this example, the first electrode on the smartwatch and the second electrode on the wristlet are both in communication with and controlled by the cardiac monitoring device.

In some embodiments, the devices described herein are configured to carry out machine learning. In some embodiments, the devices, systems, and methods described herein comprise machine learning algorithms which analyze parameter values sensed from an individual over period of time. In some embodiments, the devices, systems, and methods described herein comprise machine learning algorithms which analyze parameter values sensed from a plurality of individuals. In some embodiments, a machine learning algorithm causes the devices, systems, and methods described herein to more accurately identify or predict the presence of an arrhythmia in a given individual. For example, in some embodiments, sensed electrocardiogram data may be compared back to parameter values such as, for example, sensed heart rates and activity levels that triggered the sensing of said electrocardiograms. When, for example, sensed electrocardiograms confirm the presence of an arrhythmia, the presence of which was indicated by, for example, a discordance between other parameter values, the machine algorithm causes the device or system described herein to learn from that data. Similarly, when, for example, sensed electrocardiograms do not confirm the presence of an arrhythmia, the presence of which was indicated by, for example, a discordance between other parameter values, the machine algorithm causes the device or system described herein to learn from that data as well. That is, in some embodiments, the machine learning algorithm correlates the sensed electrocardiogram with the discordance between parameter values that caused it (i.e. the electrocardiogram) to be sensed. The presence or absence of an arrhythmia on the electrocardiogram either respectively reinforces the correlation of an arrhythmia with the discordance that caused the electrocardiogram to be sensed or contradicts the presence of a correlation of an arrhythmia with the discordance. For example, when a heart rate of 110 is sensed and simultaneously a resting activity is sensed, an electrocardiogram is caused to be sensed, and when the sensed electrocardiogram does not indicate a presence of an arrhythmia the machine learning algorithm causes the device or system as described herein to learn that for that individual a heart rate of 110 at rest does not necessarily indicate a presence of an arrhythmia. In some embodiments, the machine learning algorithm continues to cause the storing of parameter value data, such as, for example, heart rate, activity level, and heart rate variability, and compare the parameter values to the associated electrocardiogram data over time. Thus, in some embodiments, with multiple parameter values sensed over time and compared to associated electrocardiogram data, a cardiac monitoring device or system improves its ability to predict or identify the onset of arrhythmia based on a discordance between parameter values for a specific individual. In some embodiments, a machine learning algorithm may obviate the need to sense an electrocardiogram when a particular discordance is present between parameter values of a specific individual, because of an extremely high likelihood of a presence or absence of an arrhythmia based on the parameter values as determined by the machine learning algorithm.

Any of the devices, systems, and methods for cardiac monitoring described herein may comprise one or more of a smartphone, a laptop or desktop computer, a smartwatch, or a tablet computer.

Discordance Monitoring

Figure 7:
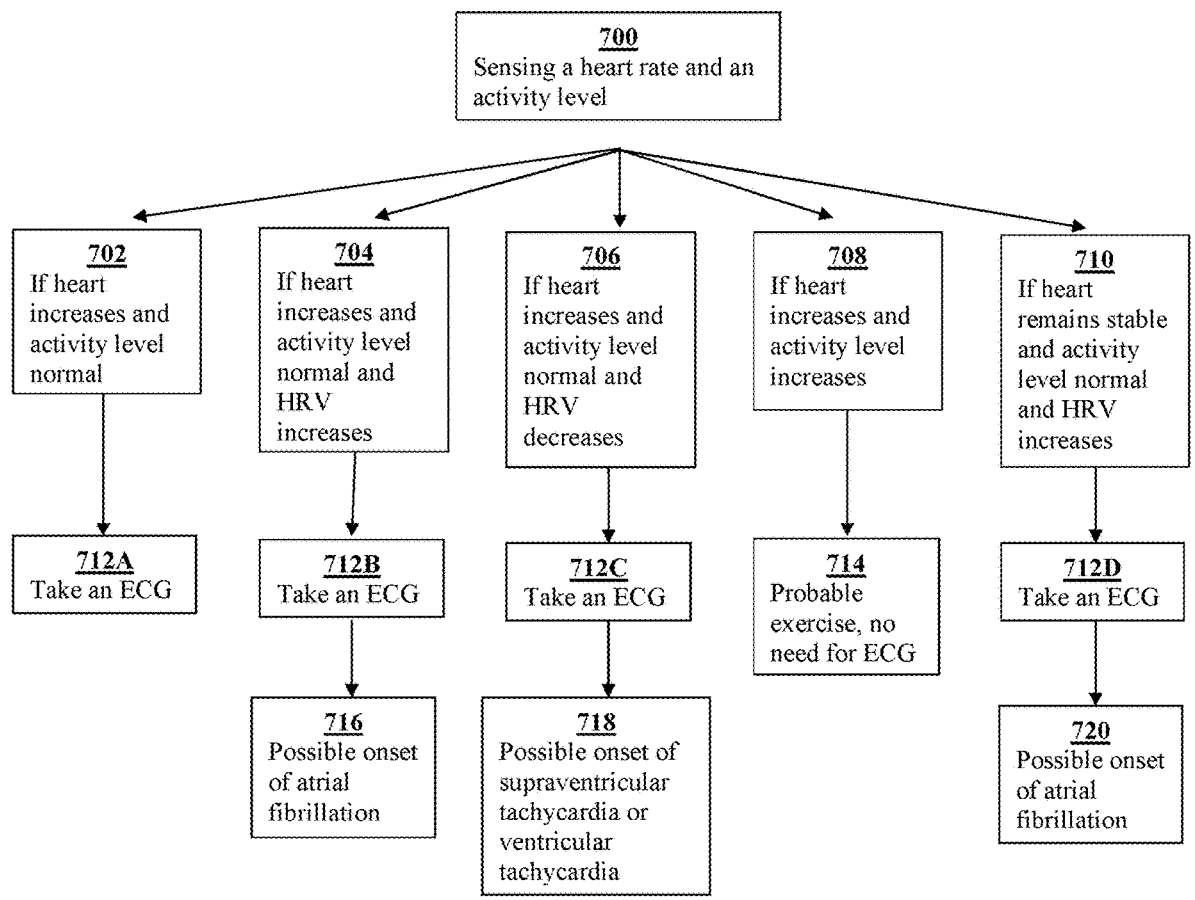
FIG. 7 shows a schematic of an algorithm for discordance monitoring.

FIG. 7 shows a schematic of an algorithm for discordance monitoring. In a step 700, a heart rate and an activity level are sensed by, for example, a device or system as described herein. In some embodiments, an activity level is sensed with a gyroscope or an accelerometer that is. Heart rate is sensed with a light based or other commonly used heart rate sensors. The device that measures the heart rate and the activity level may be the same device or more than one device. For example, a smartwatch or other wearable device may be configured to include a heart rate sensor as well as an activity level sensor.

If, as shown in a step 702, an increased heart rate is sensed together with a normal or resting activity level, the two values are determined to be in discordance by the device or system processor. That is, the elevated heart rate does no match the sensed stable activity level. Determination of the presence of the discordance is done by a processor of either the device or system as described herein. The identified discordance may indicate the presence of an arrhythmia. As such, an ECG is caused to be sensed in a step 712A. The step 712A, may, for example, comprise indicating to the user through the device or system that sensed the heart rate and activity level to contact one or more electrodes of an ECG sensing device and thus sense the ECG. The ECG sensing device may be the device or part of the system used to sense the heart rate and activity level or may be a separate device. For example, a user wearing a smartwatch with heart rate and activity level monitoring receives an audible and/or visual indication from the smartwatch to sense an ECG when a discordance is present between a sensed heart rate value and a sensed activity level value. In some embodiments, the smartwatch comprises one or more electrodes and a user contacts one electrode with the left side of their body and one electrode with the right side of their body when an indication is received to do so from the smartwatch because a discordance is present thus sensing an ECG. In some embodiments, a smartphone comprises one or more electrodes and a user contacts one electrode with the left side of their body and one electrode with the right side of their body when an indication is received to do so from the smartwatch because a discordance is present thus sensing an ECG.

If, as shown in step 704, an increased heart rate is sensed together with an increased heart rate variability, and a normal or resting activity level is sensed. The increased heart rate and HRV are in discordance with the normal or resting activity level, and a presence of a discordance is determined by the device or system processor. Once the discordance is determined, an ECG is caused to be sensed in a step 712B as, for example, described herein with respect to step 712A. As shown, in step 716, this particular discordance may be indicative of the presence of atrial fibrillation and it should be confirmed with the ECG 712B.

If, as shown in step 706, an increased heart rate is sensed together with a decreased heart rate variability and a normal or resting activity level is sensed. The increased heart rate, decreased heart rate variability, and normal or resting activity level are in discordance with each other, and a presence of a discordance is determined by the device or system processor. Once the discordance is determined, an ECG is caused to be sensed in a step 712C as, for example, described herein with respected to step 712A. As shown, in a step 718, supraventricular tachycardia may be present and it should be confirmed with the ECG of 712C.

If, as shown in a step 708, an increased heart rate is sensed together with an increased activity level, the device or system processor determines that no discordance is present, and an ECG is not recorded as the individual is probably exercising 714.

If, as shown in a step 710, a regular heart rate is sensed (e.g. 60-100 beats per minute) and an increased heart rate variability is sensed together with a normal or resting activity level. The normal heart rate, increased heart rate variability, and normal or resting activity level are in discordance with each other, and a presence of a discordance is determined by the device or system processor. Once the discordance is determined, an ECG is caused to be sensed in a step 712D as, for example, described herein with respect to step 712A. As shown, in a step 720, atrial fibrillation may be present and it should be confirmed with the ECG of 712D.

In some embodiments, a determination of the presence of a discordance is based on a comparison of two or more sensed physiologic parameters with each other. That is, for example, an elevated heart rate of 110 is compared to a resting activity level as sensed by an accelerometer which measures that the individual is traveling at 0 miles/hr. The 110 heart rate is elevated whereas the activity level of 0 miles/hr is a resting level, which indicates a discordance between the sensed heart rate and activity level. In some embodiments, a processor determines that the value of a sensed physiologic parameter is either above or below a threshold value or range of values. In some embodiments, the threshold value or range of values are deemed to be normal or resting values in the population. In some embodiments, the thresholds are specific to the biometric data of the user so that the user is, for example, age-matched or gender matched to the appropriate threshold from the general population. For example, an activity level is determined to be increased in a 70 year old user but would not be increased in a 7 year old user. Thus, a discordance is determined by qualifying if a sensed physiologic parameter is elevated, decreased, or normal (or resting) and then comparing that qualified value to a qualified value of another sensed physiologic parameter. That is, for example, a value that is qualified as either increased, decreased, or normal (or resting) is compared to a value that is also qualified as increased, decreased, or normal (or resting).

In some embodiments, there is the added step (not shown in FIG. 7) of the devices and systems described herein running machine learning algorithms so that the threshold values and ranges used to determine whether a sensed physiologic parameter is increased, decreased, normal (or resting) are adjusted to more accurately fit the user. That is, for example, a user who was determined, through ECG, to have an arrhythmia at a heart rate of 80 will have their heart rate threshold lowered so that a heart of 85 (which is normal in some) would be determined to be an increased rate. The machine learning algorithm more accurately sets the thresholds over time so that discordances are more accurately determined resulting in more accurate (and efficient) recording of ECGs in response to the determination of the presence of the discordance.

Table 1 below presents some of the information found in FIG. 7 in table form.

TABLE 1

| HR Data | Activity Level Data | HRV Data | Action |
|---|---|---|---|
| HR increases | Activity level stable | | Take an ECG, possible arrhythmia |
| HR increases | Activity level stable | HRV increases | Take an ECG, possible atrial fibrillation |
| HR increases | Activity level stable | HRV decreases | Take an ECG, possible supraventricular tachycardia or ventricular tachycardia |
| HR increases | Activity level increases | | Don't take an ECG, probable exercise |
| HR stable | Activity level stable | HRV increases | Take an ECG, possible atrial fibrillation |

While preferred embodiments of the present individual matter described herein have been shown and described herein, it will be obvious to those skilled in the art that such embodiments are provided by way of example only. Numerous variations, changes, and substitutions will now occur to those skilled in the art without departing from the individual matter described herein. It should be understood that various alternatives to the embodiments of the individual matter described herein described herein may be employed in practicing the individual matter described herein. It is intended that the following claims define the scope of the individual matter described herein and that methods and structures within the scope of these claims and their equivalents be covered thereby.

What is claimed is:

1. A method of cardiac monitoring, comprising:
sensing an activity level of a user with a first sensor on a smartwatch worn by the user;
when the activity level is resting, sensing a heart rate parameter of the user with a second sensor on the smartwatch;
determining, by a processing device, that a discordance is present between the activity level value and the heart rate parameter;
based on the presence of the discordance, indicating to the user, using the smartwatch, a possibility of an arrhythmia being present; and
receiving electric signals of the user from an electrocardiogram sensor ("ECG") on the smartwatch to confirm a presence of the arrhythmia, wherein the ECG sensor comprises a first electrode and a second electrode.

2. The method according to claim 1, wherein the heart rate parameter comprises an indication of a heart rate variability, and wherein the arrhythmia is atrial fibrillation.

3. The method according to claim 1, wherein the heart rate parameter comprises an indication of a heart rate variability and a heart rate value, and wherein the arrhythmia is atrial fibrillation.

4. The method according to claim 1, wherein the heart rate parameter comprises an indication a heart rate value, and wherein the arrhythmia is atrial fibrillation.

5. The method according to claim 1, wherein indicating to the user further comprises: instructing the user to record an ECG using the smartwatch.

6. The method according to claim 1, wherein the arrhythmia is selected from a group consisting of atrial fibrillation, supraventricular tachycardia, and ventricular tachycardia.

7. The method according to claim 1, wherein the heartrate parameter is a PPG signal.

8. The method according to claim 7, wherein the heart rate parameter is a heartrate variability ("HRV") value, wherein the HRV value is derived from the PPG signal.

9. The method according to claim 7, wherein the heart rate parameter is a heartrate, wherein the heartrate is derived from the PPG signal.

10. The method according to claim 1 further comprising: displaying an ECG rhythm strip from the electric signals on the smartwatch.

11. The method according to claim 1, wherein the first electrode is located on the smartwatch in a location where the first electrode contacts a first side of the user's body while the user wears the smartwatch, and the second electrode is located on the smartwatch in a location where the user must actively contact the second electrode with a second side of the user's body opposite from the first side.

12. A smartwatch, comprising:
a processor;
a first sensor configured to sense an activity level value of a user, wherein the first sensor is coupled to the processor;
a photoplethysmogram ("PPG") sensor configured to sense a heart rate parameter of the user when the activity level value is resting, wherein the PPG sensor is coupled to the processor;
an electrocardiogram ("ECG") sensor configured to sense electrical signals of a heart, wherein the ECG sensor comprises a first electrode and a second electrode, and wherein the ECG sensor is coupled to the processor; and
a non-transitory computer readable storage medium encoded with a computer program including instructions executable by the processor to cause the processor to:
determine if a discordance is present between the activity level value of the user and the heart rate parameter of the user;
based on the presence of the discordance, indicate to the user a possibility of an arrhythmia being present; and
receive electric signals of the user from the ECG sensor to confirm the presence of the arrhythmia.

13. The smartwatch or wristlet according to claim 12, wherein the heart rate parameter comprises an indication of a heart rate variability, and wherein the arrhythmia is atrial fibrillation.

14. The smartwatch or wristlet according to claim 12, wherein the heart rate parameter comprises an indication of a heart rate variability and a heart rate value, and wherein the arrhythmia is atrial fibrillation.

15. The smartwatch or wristlet according to claim 12, wherein the heart rate parameter comprises an indication of a heart rate value, and wherein the arrhythmia is atrial fibrillation.

16. The smartwatch or wristlet according to claim 12, wherein indicating to the user further comprises: instructing the user to record an ECG using the ECG sensor.

17. The smartwatch or wristlet according to claim 12, wherein the arrhythmia is selected from a group consisting of atrial fibrillation, supraentricular tachycardia, and ventricular tachycardia.

18. The smartwatch according to claim 12, wherein the heart rate parameter is a PPG signal.

19. The smartwatch according to claim 18, wherein the heart rate parameter is a heartrate variability ("HRV") value, wherein the HRV value is derived from the PPG signal.

20. The smartwatch according to claim 18, wherein the heart rate parameter is a heartrate, wherein the heartrate is derived from the PPG signal.

21. The smartwatch according to claim 12, the processor further to: display an ECG rhythm strip from the electric signals.

22. The smartwatch according to claim 12, wherein the PPG sensor is located on a back of the smartwatch.

23. The smartwatch according to claim 12, wherein the first electrode is located on the smartwatch where the first electrode contacts a first side of the user's body while the user wears the smartwatch, and the second electrode is located on the smartwatch where the user must actively contact the second electrode with a second side of the user's body opposite from the first side.

* * * * *

UNITED STATES PATENT AND TRADEMARK OFFICE
CERTIFICATE OF CORRECTION

PATENT NO. : 10,638,941 B2  
APPLICATION NO. : 16/158112  
DATED : May 5, 2020  
INVENTOR(S) : David E. Albert et al.

Page 1 of 1

It is certified that error appears in the above-identified patent and that said Letters Patent is hereby corrected as shown below:

On the Title Page

Under item (72), please add the inventors as shown below:
(72) Inventors: Fei WANG, San Francisco, CA (US)
       Euan THOMSON, Los Gatos, CA (US)
       Iman ABUZEID, San Francisco, CA (US)

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*